(12) United States Patent
Stafford (10) Patent No.: US 8,333,714 B2
(45) Date of Patent: Dec. 18, 2012

(54) METHOD AND SYSTEM FOR PROVIDING AN INTEGRATED ANALYTE SENSOR INSERTION DEVICE AND DATA PROCESSING UNIT

(75) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/530,472

(22) Filed: Sep. 10, 2006

(65) Prior Publication Data

US 2008/0097246 A1 Apr. 24, 2008

(51) Int. Cl.
*B65D 81/00* (2006.01)
(52) U.S. Cl. .................. 600/584; 600/347; 141/329
(58) Field of Classification Search .............. 600/584, 600/347; 141/329
See application file for complete search history.

(56) References Cited

U.S. PATENT DOCUMENTS

| | | |
|---|---|---|
| 3,123,790 A | 3/1964 | Tyler |
| 3,260,656 A | 7/1966 | Ross, Jr. |
| 3,581,062 A | 5/1971 | Aston |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |

(Continued)

FOREIGN PATENT DOCUMENTS

CA 2291105 12/1998

(Continued)

OTHER PUBLICATIONS

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.

(Continued)

*Primary Examiner* — Max Hindenburg
*Assistant Examiner* — Renee Danega
(74) *Attorney, Agent, or Firm* — Jackson & Co., LLP (57) ABSTRACT

Method and apparatus for providing an integrated analyte sensor and data processing unit assembly is provided.

35 Claims, 5 Drawing Sheets

U.S. PATENT DOCUMENTS

| | | | |
|---|---|---|---|
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |

| Patent No. | Date | Inventor |
|---|---|---|
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A * | 11/1994 | Novacek et al. ............ 604/110 |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Matcalf et al. |
| 5,545,191 A | 8/1996 | Mann et al. |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,942,979 A | 8/1999 | Luppino |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,368 A * | 2/2000 | Gavronsky et al. ........... 606/189 |
| 6,024,699 A | 2/2000 | Surwit et al. |
| 6,026,321 A | 2/2000 | Miyata et al. |
| 6,049,727 A | 4/2000 | Crothall |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |

| | | |
|---|---|---|
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,478,736 B1 | 11/2002 | Mault |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,551,494 B1 | 4/2003 | Heller et al. |
| 6,551,496 B1 | 4/2003 | Moles et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 * | 8/2003 | Bobroff et al. ................ 604/136 |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 * | 5/2005 | McIvor et al. ................ 600/347 |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |

| Patent/Publication No. | Date | Inventor(s) |
|---|---|---|
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,736,344 B2 | 6/2010 | Moberg et al. |
| 7,763,042 B2 | 7/2010 | Iio et al. |
| 7,822,454 B1 | 10/2010 | Alden et al. |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0198444 A1 | 12/2002 | Uchigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1* | 1/2004 | Flaherty et al. ............... 600/573 |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0147996 A1 | 7/2004 | Miazga et al. |
| 2004/0158207 A1 | 8/2004 | Hunn et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0267327 A1 | 12/2005 | Iizuka et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0004303 A1* | 1/2006 | Weidenhaupt et al. ....... 600/583 |
| 2006/0010098 A1 | 1/2006 | Goodnow et al. |
| 2006/0015020 A1 | 1/2006 | Neale et al. |
| 2006/0015024 A1* | 1/2006 | Brister et al. ................. 600/345 |
| 2006/0016700 A1 | 1/2006 | Brister et al. |
| 2006/0019327 A1 | 1/2006 | Brister et al. |
| 2006/0020186 A1* | 1/2006 | Brister et al. ................. 600/345 |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |

| Publication No. | Date | Inventor |
|---|---|---|
| 2006/0247508 A1 | 11/2006 | Fennell |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1* | 3/2007 | Shah et al. ............ 600/365 |
| 2007/0078320 A1 | 4/2007 | Stafford |
| 2007/0078321 A1 | 4/2007 | Mazza et al. |
| 2007/0078322 A1 | 4/2007 | Stafford |
| 2007/0095661 A1 | 5/2007 | Wang et al. |
| 2007/0106135 A1 | 5/2007 | Sloan et al. |
| 2007/0110124 A1 | 5/2007 | Zaragoza et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0112848 A1 | 5/2008 | Huffstodt et al. |
| 2008/0133702 A1 | 6/2008 | Sharma et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262330 A1 | 10/2008 | Reynolds et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088787 A1 | 4/2009 | Koike et al. |
| 2009/0099436 A1 | 4/2009 | Brister et al. |
| 2009/0102678 A1 | 4/2009 | Stafford et al. |
| 2009/0105569 A1 | 4/2009 | Stafford |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |

| | | | |
|---|---|---|---|
| 2010/0030484 A1 | 2/2010 | Brauker et al. | |
| 2010/0030485 A1 | 2/2010 | Brauker et al. | |
| 2010/0036215 A1 | 2/2010 | Goode, Jr. et al. | |
| 2010/0036216 A1 | 2/2010 | Goode, Jr. et al. | |
| 2010/0036222 A1 | 2/2010 | Goode, Jr. et al. | |
| 2010/0036223 A1 | 2/2010 | Goode, Jr. et al. | |
| 2010/0036225 A1 | 2/2010 | Goode, Jr. et al. | |
| 2010/0041971 A1 | 2/2010 | Goode, Jr. et al. | |
| 2010/0045465 A1 | 2/2010 | Brauker et al. | |
| 2010/0049014 A1 | 2/2010 | Funderburk et al. | |
| 2010/0049024 A1 | 2/2010 | Saint et al. | |
| 2010/0063373 A1 | 3/2010 | Kamath et al. | |
| 2010/0076283 A1 | 3/2010 | Simpson et al. | |
| 2010/0081908 A1 | 4/2010 | Dobbles et al. | |
| 2010/0081910 A1 | 4/2010 | Brister et al. | |
| 2010/0087724 A1 | 4/2010 | Brauker et al. | |
| 2010/0096259 A1 | 4/2010 | Zhang et al. | |
| 2010/0099970 A1 | 4/2010 | Shults et al. | |
| 2010/0099971 A1 | 4/2010 | Shults et al. | |
| 2010/0100113 A1 | 4/2010 | Iio et al. | |
| 2010/0113897 A1 | 5/2010 | Brenneman et al. | |
| 2010/0119693 A1 | 5/2010 | Tapsak et al. | |
| 2010/0121169 A1 | 5/2010 | Petisce et al. | |
| 2010/0174157 A1 | 7/2010 | Brister et al. | |
| 2010/0185069 A1 | 7/2010 | Brister et al. | |
| 2010/0204653 A1 | 8/2010 | Gryn et al. | |
| 2010/0212583 A1 | 8/2010 | Brister et al. | |
| 2010/0217105 A1 | 8/2010 | Yodfat et al. | |
| 2010/0262201 A1 | 10/2010 | He et al. | |
| 2010/0331642 A1 | 12/2010 | Bruce et al. | |
| 2011/0040256 A1 | 2/2011 | Bobroff et al. | |
| 2011/0040263 A1 | 2/2011 | Hordum et al. | |
| 2011/0077490 A1 | 3/2011 | Simpson et al. | |
| 2011/0137257 A1 | 6/2011 | Gyrn et al. | |
| 2011/0178461 A1 | 7/2011 | Chong et al. | |

FOREIGN PATENT DOCUMENTS

| | | |
|---|---|---|
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004-520898 | 7/2004 |
| WO | WO-96/39977 | 5/1996 |
| WO | WO-96/25089 | 8/1996 |
| WO | WO-96/35370 | 11/1996 |
| WO | WO 98/56293 * | 5/1998 |
| WO | WO-98/35053 | 8/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/084534 | 9/2005 |
| WO | WO-2005/089103 | 9/2005 |
| WO | WO-2006/042811 | 4/2006 |
| WO | WO 2006/108809 * | 4/2006 |
| WO | WO-2006/108809 | 10/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/120363 | 10/2007 |
| WO | WO-2007/143225 | 12/2007 |
| WO | WO-2008/031110 | 3/2008 |
| WO | WO-2008/039944 | 4/2008 |
| WO | WO-2008/051920 | 5/2008 |
| WO | WO-2008/051924 | 5/2008 |
| WO | WO-2008/065646 | 6/2008 |
| WO | WO-2008/103620 | 8/2008 |
| WO | WO-2008/133702 | 11/2008 |
| WO | WO-2008/150917 | 12/2008 |
| WO | WO-2009/062675 | 5/2009 |
| WO | WO-2010/112521 | 10/2010 |
| WO | WO-2011/002815 | 1/2011 |

OTHER PUBLICATIONS

Schmidt, F. J., et al., "Calibration of a Wearable Glucose Sensor", *The International Journal of Artificial Organs*, vol. 15, No. 1, 1992, pp. 55-61.

European Patent Application No. EP-07842173.2, Extended European Search Report mailed Dec. 29, 2010.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Alcock, S. J., et al., "Continuous Analyte Monitoring to Aid Clinical Practice", *IEEE Engineering in Medicine and Biology Magazine*, 1994, pp. 319-325.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Gregg, B. A., et al., "Cross-Linked Redox Gels Containing Glucose Oxidase for Amperometric Biosensor Applications", *Analytical Chemistry*, vol. 62, No. 3, 1990, pp. 258-263.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Heller, A., "Electrical Connection Enzyme Redox Centers to Electrodes", *Journal of Physical Chemistry*, vol. 96, No. 9, 1990, pp. 3579-3587.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Maidan, R., et al., "Elimination of Electrooxidizable Interferant-Produced Currents in Amperometric Biosensors", *Analytical Chemistry*, vol. 64, No. 23, 1992, pp. 2889-2896.

Mastrototaro, J. J., et al., "An Electroenzymatic Glucose Sensor Fabricated on a Flexible Substrate", *Sensors and Actuators B*, vol. 5, 1991, pp. 139-144.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.

Poitout, V., et al., "In Vitro and In Vivo Evaluation in Dogs of a Miniaturized Glucose Sensor", *ASAIO Transactions*, vol. 37, No. 3, 1991, pp. M298-M300.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.
Ye, L., et al., "High Current Density 'Wired' Quinoprotein Glucose Dehydrogenase Electrode", *Analytical Chemistry*, vol. 65, No. 3, 1993, pp. 238-241.
International Search Report and Written Opinion of the International Searching Authority for PCT Application No. PCT/US2007/078065 filed Sep. 10, 2007 to Abbott Diabetes Care, Inc.
Armour, J. C., et al., "Application of Chronic Intravascular Blood Glucose Sensor in Dogs", *Diabetes*, vol. 39, 1990, pp. 1519-1526.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", pp. 250, 2002.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 16 Pages, 2001.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.

\* cited by examiner

METHOD AND SYSTEM FOR PROVIDING AN INTEGRATED ANALYTE SENSOR INSERTION DEVICE AND DATA PROCESSING UNIT

BACKGROUND

Analyte monitoring systems generally include a sensor such as a subcutaneous analyte sensor, at least a portion of which is inserted under the skin for fluid contact with interstitial fluid, for detecting analyte levels such as glucose levels, a transmitter (such as an RF transmitter) in communication with the sensor and configured to receive the sensor signals and to transmit them to a corresponding receiver unit by for example, using RF data transmission protocol. The receiver may be operatively coupled to a glucose monitor that performs glucose related calculations and data analysis.

The transmitter is in signal communication with the sensor. Generally, the sensor is configured to detect and measure the glucose levels of the patient over a predetermined period of time, and the transmitter is configured to transmit data corresponding to or associated with the measured glucose levels over the predetermined period of time for further analysis. To initially deploy the sensor so that the sensor electrodes are in fluid contact with the patient's analyte fluids, a separate deployment mechanism such as a sensor inserter or introducer is used. More specifically, the introducer includes a sharp needle shaped inserter that is configured to pierce through the skin of the patient and substantially concurrently guide the sensor through the patient's skin so as to place at least a portion of the sensor in fluid contact with the target biological fluid of the patient.

The inserter is typically used only during the sensor insertion process, and once the sensor is properly and accurately positioned, the inserter and the introducer are discarded. This requires a level of care as the inserter is sharp and may damage other parts of the patient's skin if not properly handled. Further, since the tip of the inserter has come into fluid contact with the patient's biological fluids, it is important to take particular precautions in the handling of the inserter.

Further, to minimize data errors in the continuous or semi-continuous monitoring system, it is important to properly insert the sensor through the patient's skin and securely retain the sensor during the time that the sensor is configured to detect analyte levels. Additionally, for the period of continuous or semi-continuous monitoring which can include, for example, 3 days, 5 days or 7 days, it is important to have the transmitter in proper signal contact with the analyte sensor so as to minimize the potential errors in the monitored data.

In view of the foregoing, it would be desirable to have method and apparatus for providing simple, easy to handle and accurate sensor introduction and retention mechanism for use in an analyte monitoring system. More specifically, it would be desirable to have method and apparatus that minimizes the number of components which the patient has to handle, and which also reduces the number of required steps to properly and accurately position the analyte sensor in fluid contact with the patient's analytes.

SUMMARY OF THE INVENTION

An integrated assembly in accordance with one embodiment of the present invention includes a housing, a data processing unit substantially disposed within the housing, an introducer removably coupled to the housing, at least a portion of the introducer disposed within the housing, and an analyte sensor coupled to the housing, a first portion of the analyte sensor configured for subcutaneous placement and in fluid contact with an interstitial fluid of a subject, and a second portion of the analyte sensor disposed within the housing and in electrical communication with the data processing unit.

In the manner described, within the scope of the present invention, the integrated analyte sensor and data processing unit assembly in accordance with the various embodiments is configured to integrate an analyte sensor, a sensor introducer mechanism, and a data processing device into a single assembly which is may be disposable, and which allows for simple and accurate sensor deployment to the desired subcutaneous position, and that may be easily operated using one hand by the user or the patient.

These and other features and advantages of the present invention will be understood upon consideration of the following detailed description of the invention and the accompanying drawings.

DETAILED DESCRIPTION

In accordance with the various embodiments of the present invention, there is provided an integrated analyte sensor delivery and data processing unit for subcutaneous placement of an analyte sensor for fluid contact with an analyte of a subject for analyte monitoring, and data processing associated with the monitored analyte levels. More specifically, the integrated analyte sensor delivery and data processing unit in accordance with one embodiment of the present invention provides simple, easy to use analyte sensor placement for analyte monitoring and associated data processing without a direct line of sight visual aid, and also, which may be easily performed without the use of both hands.

Figure 1:
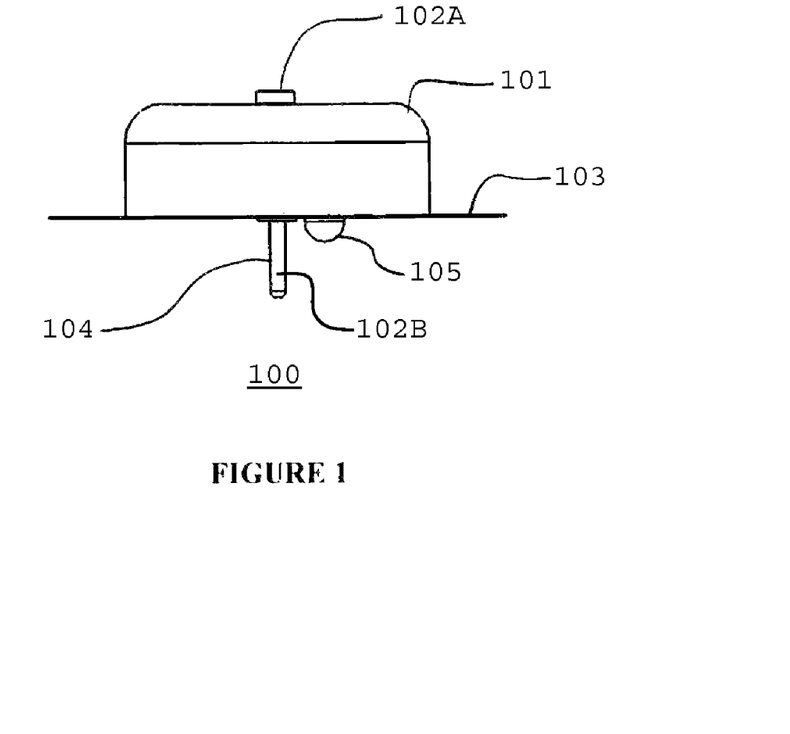
FIG. 1 illustrates a side view of the overall assembly of an integrated analyte sensor delivery and data processing unit in accordance with one embodiment of the present invention.

FIG. 1 illustrates a side view of the overall assembly of an integrated analyte sensor delivery and data processing unit in accordance with one embodiment of the present invention. Referring to FIG. 1, in one embodiment, an integrated analyte sensor delivery and data processing unit assembly 100 includes a data processing unit 101 provided on an upper surface of an adhesive patch 103 as shown. The adhesive patch 103 in one embodiment is provided with an adhesive material, such as, for example, polyester or acrylic based adhesives or any other suitable material which are biocompatible providing sufficient adhesive strength, on its bottom surface that is configured to securely attach the adhesive patch 103 and the data processing unit 101 on a surface of a subject such as the skin of a patient.

Referring to FIG. 1, also provided is a temperature module 105 to be in physical contact with the surface of the subject to, among others, detect the temperature, as further discussed in further detail below in conjunction with temperature measurement section 703 of FIG. 7. Referring again to FIG. 1, the integrated sensor delivery and data processing unit assembly 100 in one embodiment also includes an introducer having an upper portion 102A and a lower portion 102B. The upper and lower portions 102A, 102B of the introducer in one embodiment is coupled to the housing of the data processing unit 101 such that the upper portion 102A of the introducer protrudes from an upper surface of the data processing unit 101, while the lower portion 102B of the introducer is configured to protrude downwardly from the bottom surface of the data processing unit 101 as can be seen in FIG. 1.

As shown in FIG. 1, the upper portion 102A of the introducer is configured to guide the user to insert the introducer through the surface of the subject such as the skin of the patient. Thus, the upper portion 102A of the introducer in one embodiment is provided with a larger surface area (that is, for example, a larger diameter) to apply force thereon, while the lower portion 102B of the introducer is configured with a sharp tip to facilitate puncturing or piercing through the surface of the subject such as the skin of the patient.

Additionally, in one aspect, there is provided a guard segment 104 in the integrated analyte sensor and data processing unit assembly 100 such that the guard segment 104 is configured to substantially cover the lower portion 102B of the introducer. In one embodiment, the guard segment 104 is configured as a protective needle guard so as to maintain the lower portion 102B of the introducer in a substantially sterile environment prior to subcutaneous placement through the surface of the subject such as the skin of the patient. Moreover, in one aspect, the guard segment 104 is configured to protect the sharp edge of the lower portion 102B of the introducer from inadvertent contact with the subject, for example, prior to the subcutaneous deployment of the analyte sensor to avoid, for example, contamination of the lower portion 102B of the introducer, or potential injury from the sharp edge of the power portion 102B of the introducer.

Figure 2:
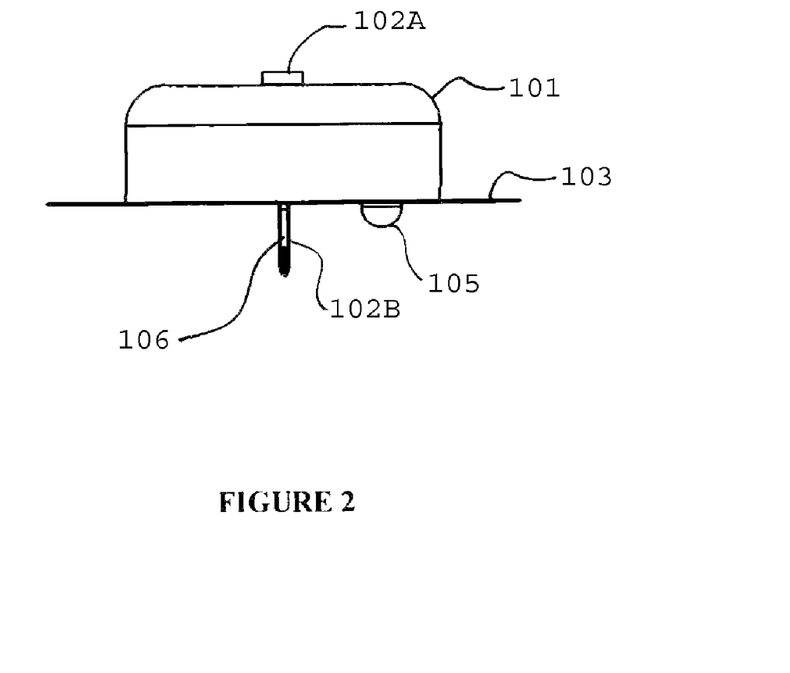
FIG. 2 illustrates a side view of the integrated analyte sensor delivery and data processing unit of FIG. 1 without a protective guard in accordance with one embodiment of the present invention.

More specifically, FIG. 2 illustrates a side view of the integrated analyte sensor delivery and data processing unit of FIG. 1 without a guard segment in accordance with one embodiment of the present invention. Referring to FIG. 2, with the guard segment 104 removed, it can be seen that in one embodiment, analyte sensor 106 is provided in the integrated analyte sensor delivery and data processing unit 100 such that the at least a portion of the analyte sensor 106 is disposed within the lower portion 102B of the introducer.

In one embodiment, the patient or the user of the integrated analyte sensor delivery and data processing unit assembly 100 removes the guard segment 104 to expose the lower portion 102B of the introducer, and thereafter, places the entire analyte sensor delivery and data processing unit assembly 100 on the surface of the subject such as the skin layer of the patient with sufficient force applied on the upper surface of the data processing unit 101 such that the lower portion 102B of the introducer is pierced through the skin layer of the patient. Thereafter, the introducer may be removed to detach or decouple from the data processing unit 101 by, for example, pulling at the upper portion 102A of the introducer, thereby withdrawing the introducer from the patient and separating from the data processing unit 101, while retaining the analyte sensor 106 (FIG. 2) in position in fluid contact with the patient's analyte.

Referring again to FIGS. 1 and 2, in one embodiment, the bottom layer of the adhesive patch 103 may be provided with a protective layer (not shown) which the patient or the user of the integrated analyte sensor delivery and data processing unit assembly 100 removes (for example, by peeling off to detach from the bottom surface of the adhesive patch 103 and thus exposing the adhesive material on the bottom surface of the adhesive patch 103) prior to subcutaneously positioning the analyte sensor in the patient. For example, in one embodiment, the guard segment 104 may be first removed and the protective layer removed before use, or alternatively, the removal of the protective layer may be configured to remove or detach the guard segment 104 therewith. In an alternate embodiment, the protective layer and the guard segment 104 may be formed as a single integrated unit for ease of use.

Figure 3A:
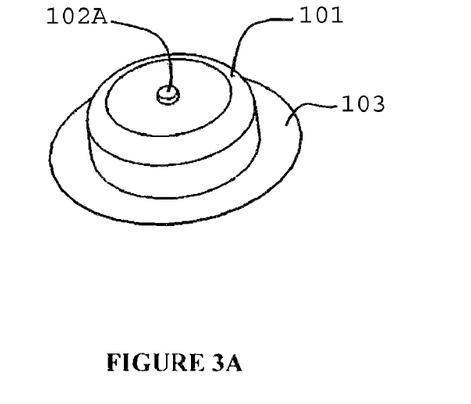
FIGS. 3A-3C illustrate a perspective view, a top planar view and a bottom planar view, respectively of the integrated analyte sensor delivery and data processing unit of FIG. 1 in accordance with one embodiment of the present invention.
Figure 3B:
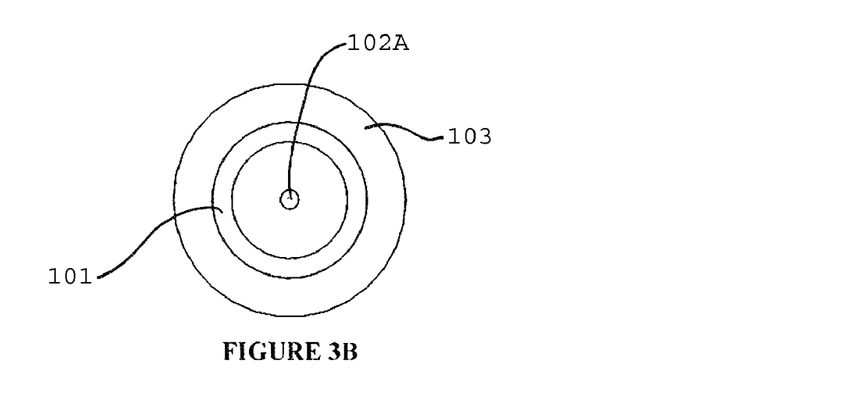
Figure 3C:
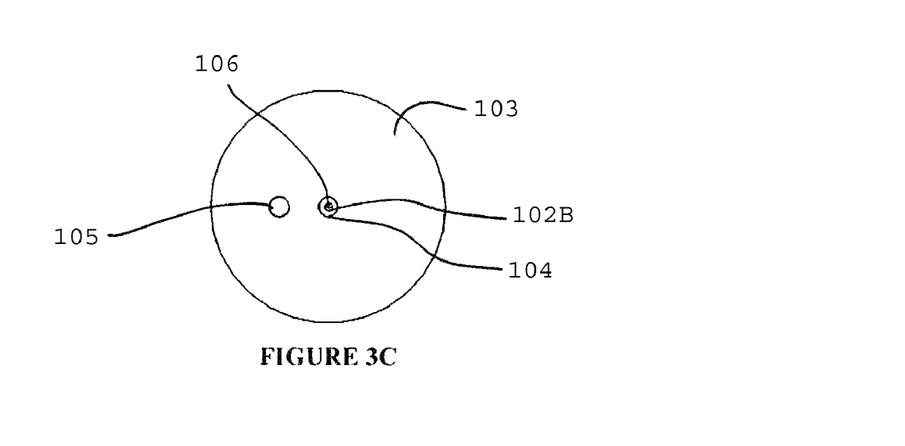

FIGS. 3A-3C illustrate a perspective view, a top planar view and a bottom planar view, respectively of the integrated analyte sensor delivery and data processing unit of FIG. 1 in accordance with one embodiment of the present invention.

Figure 4A:
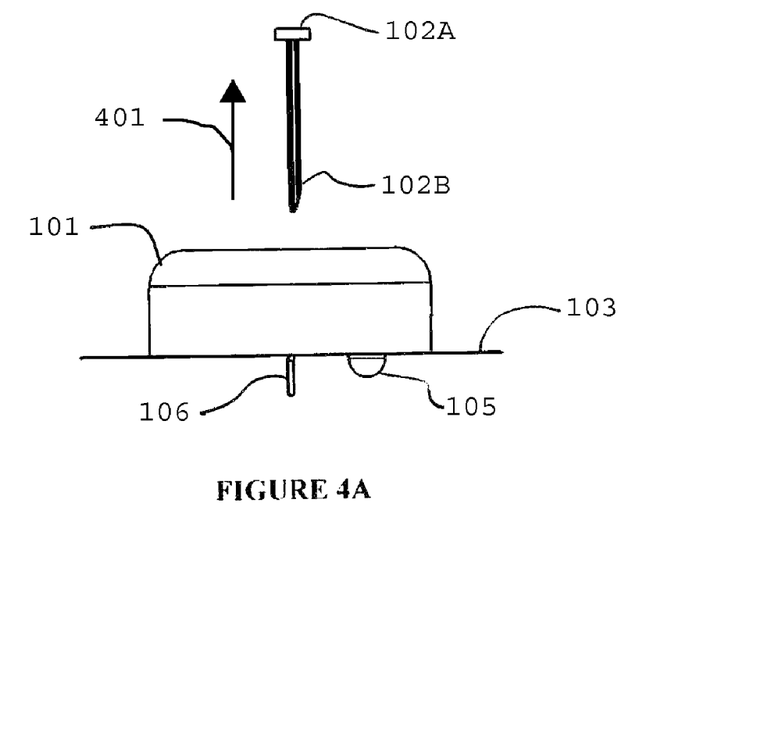
FIG. 4A illustrates the integrated analyte sensor delivery and data processing unit of FIG. 1 with the introducer removed in accordance with one embodiment.
Figure 4B:
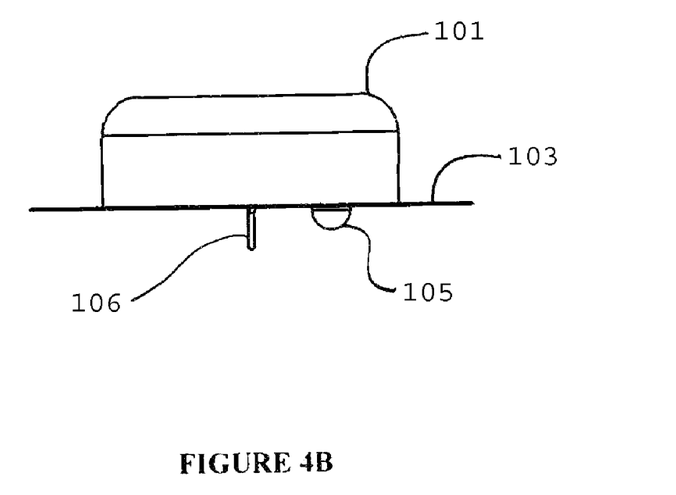
FIG. 4B illustrates the integrated analyte sensor delivery and data processing unit without the introducer in accordance with one embodiment of the present invention.

Referring now to FIG. 4A, the removal of the introducer is shown. More specifically, FIG. 4A illustrates the integrated analyte sensor delivery and data processing unit of FIG. 1 with the introducer removed, and FIG. 4B illustrates the integrated analyte sensor delivery and data processing unit without the introducer in accordance with one embodiment of the present invention. That is, in one embodiment, upon placement of the integrated analyte sensor delivery and data processing unit assembly 100 on the skin surface of the patient, for example, the patient retracts or pulls the introducer substantially at the upper portion 102A in the direction substantially perpendicular and away from the data processing unit 101 as shown by the directional arrow 401.

When the introducer is removed, in one embodiment, the entire introducer including the upper portion 102A and the lower portion 102B is withdrawn from the housing of the data processing unit 101 to completely separate from the data processing unit. Moreover, the portion of the analyte sensor 106 is retained in the subcutaneous position so as to maintain fluid contact with the patient's analyte. In one embodiment, the housing of the transmitter unit 101 is provided with a self-sealing aperture (not shown) through which the introducer may be removed, such that, when the introducer is withdrawn, there is no opening or aperture on the data processing unit 101 housing where moisture or contaminant may compromise the functions and operations of the data processing unit 101. Optionally, while not shown, a protective layer may be provided over the integrated analyte sensor delivery and data processing unit 100 upon positioning on the skin of the patient to provide protection from water, moisture or any other potential contaminants potentially damaging the integrated analyte sensor delivery and data processing unit 100.

Figure 5A:
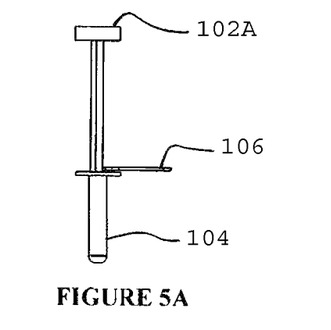
FIG. 5A illustrates the introducer and the analyte sensor assembly with the protective guard in accordance with one embodiment of the present invention.
Figure 5B:
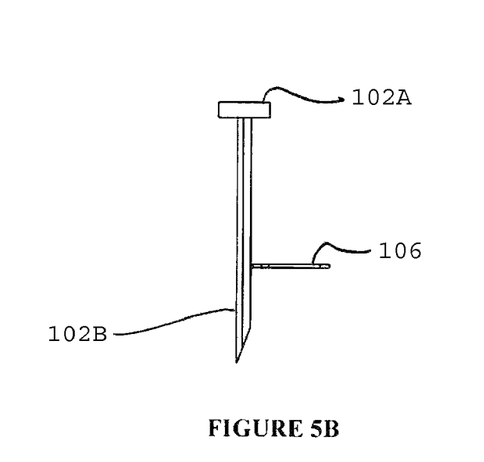
FIGS. 5B-5C illustrate a side view and a perspective view, respectively, of the introducer and analyte sensor assembly in accordance with one embodiment of the present invention.
Figure 5C:
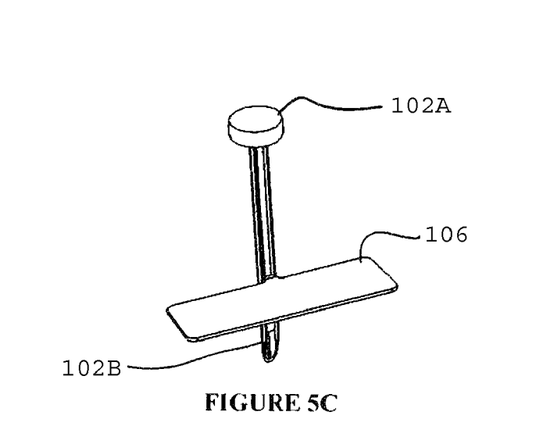

FIG. 5A illustrates the introducer and the analyte sensor assembly with the protective guard, and FIGS. 5B-5C illustrate a side view and a perspective view, respectively, of the introducer and analyte sensor assembly in accordance with one embodiment of the present invention. As shown in the Figures, the integrated analyte sensor delivery and data processing unit 100 in one embodiment may be pre-assembled as a single integrated unit with the analyte sensor 106 in electrical contact with the data processing unit 101, and further, where a portion of the analyte sensor 106 is disposed within the lower portion 102B of the introducer such that, the user or patient may easily, and accurately position the analyte sensor 106 under the skin layer to establish fluid contact with the patient's analyte, and thereafter, to provide the detected analyte levels from the analyte sensor 106 to the data processing unit 101.

Figure 6:
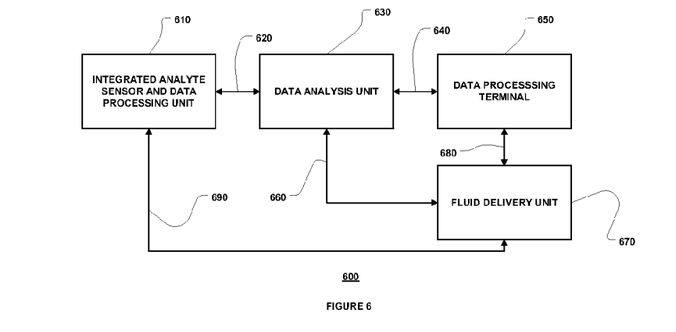
FIG. 6 illustrates a block diagram of an analyte monitoring system with integrated analyte sensor delivery and data processing unit in accordance with one embodiment of the present invention.

FIG. 6 illustrates a block diagram of an analyte monitoring system with integrated analyte sensor delivery and data processing unit in accordance with one embodiment of the present invention. Referring to FIG. 6, a data monitoring and management system 600 such as, for example, an analyte (e.g., glucose) monitoring and management system in accordance with one embodiment of the present invention is shown. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The data monitoring and management system 600 in one embodiment includes an integrated analyte sensor and data processing unit 610, a data analysis unit 630 which is configured to communicate with the integrated analyte sensor and data processing unit 610 via a communication link 620. The data analysis unit 630 may be further configured to transmit and/or receive data to and/or from a data processing terminal 650 via communication link 640. The data processing terminal 650 in one embodiment may be configured for evaluating the data received by the data analysis unit 630.

Referring again to FIG. 6, also shown is a fluid delivery unit 670 which is operatively coupled to the data processing terminal 650 via communication link 680, and further operatively coupled to the data analysis unit 630 via communication link 660, and also, operatively coupled to the integrated analyte sensor and data processing unit 610 via communication link 690. In one embodiment, the fluid delivery unit 670 may include an external or implantable infusion device such as an insulin infusion pump, or the like, which may be configured to administer insulin to patients, and which may be configured to determine suitable modifications or updates to the medication dispensing profile based on data received from one or more of the integrated analyte sensor and data processing unit 610, data analysis unit 630, or data processing terminal 650, for example, for administering and modifying basal profiles, as well as for determining appropriate boluses for administration based on, among others, the detected analyte levels received from the integrated analyte sensor and data processing unit 610.

Furthermore, referring again to FIG. 6, the one or more of the communication links 620, 640, 680, and 690 may be configured as one or more of a wired or a wireless communication link, for example, including but not limited to RS232 cable connection, a Universal Serial Bus (USB) connection, an RF communication link, an infrared communication link, a Bluetooth enabled communication link, an 802.11x wireless communication link, or an equivalent wireless communication protocol which would allow secure, wireless communication of several units (for example, per HIPPA requirements) while avoiding potential data collision and interference.

Moreover, it will be appreciated by one of ordinary skill in the art that the data monitoring and management system 600 may include one or more integrated analyte sensor and data processing unit 610, one or more data analysis unit 630, one or more fluid delivery unit 670 and one or more data processing terminal 650. In addition, the one or more integrated analyte sensor and data processing unit 610, one or more data analysis unit 630, one or more fluid delivery unit 670 and one or more data processing terminal 650 may be in communication with a remote site over a data network such as the internet for transmitting and/or receiving information associated with the functions and operations of each device. For example, the one or more integrated analyte sensor and data processing unit 610, one or more data analysis unit 630, one or more fluid delivery unit 670 and one or more data processing terminal 650 may be in communication with a data network such as the Internet for retrieving and/or transmitting data from a remote server terminal.

Furthermore, in one embodiment, in a multi-component environment, each device is configured to be uniquely identified by each of the other devices in the system so that communication conflict is readily resolved between the various components within the data monitoring and management system 100.

In one embodiment of the present invention, the sensor 106 is physically positioned in or on the body of a user whose analyte level is being monitored. The sensor 106 may be configured to continuously sample the analyte level of the user and convert the sampled analyte level into a corresponding data signal for transmission by the data processing unit 101. More specifically, in one embodiment, the data processing unit 101 may be configured to perform data processing such as filtering and encoding of data signals, each of which corresponds to a sampled analyte level of the user, for transmission to the data analysis unit 630 via the communication link 620.

In one embodiment, the communication link 620 may be configured as a one-way RF communication path from the integrated analyte sensor and data processing unit 610 to the data analysis unit 630. In such embodiment, the data processing unit 101 of the integrated analyte sensor and data processing unit 610 is configured to transmit the sampled data signals received from the sensor 106 without acknowledgement from the data analysis unit 630 that the transmitted sampled data signals have been received. For example, the data processing unit 101 may be configured to transmit the encoded sampled data signals at a fixed rate (e.g., at one minute intervals) after the completion of the initial power on procedure. Likewise, the data analysis unit 630 may be configured to detect the encoded sampled data signals transmitted from the data processing unit 101 at predetermined time intervals. Alternatively, the communication link 620 may be configured with a bi-directional RF (or otherwise) communication between the data processing unit 101 and the data analysis unit 630.

Referring again to FIG. 6, in one embodiment, the data processing terminal 650 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 650 may further be connected to a remote data network such as over the Internet (not shown) for storing, retrieving and updating data corresponding to the detected analyte level of the user and/or therapy related information such as medication delivery profiles prescribed by a physician, for example.

Figure 7:
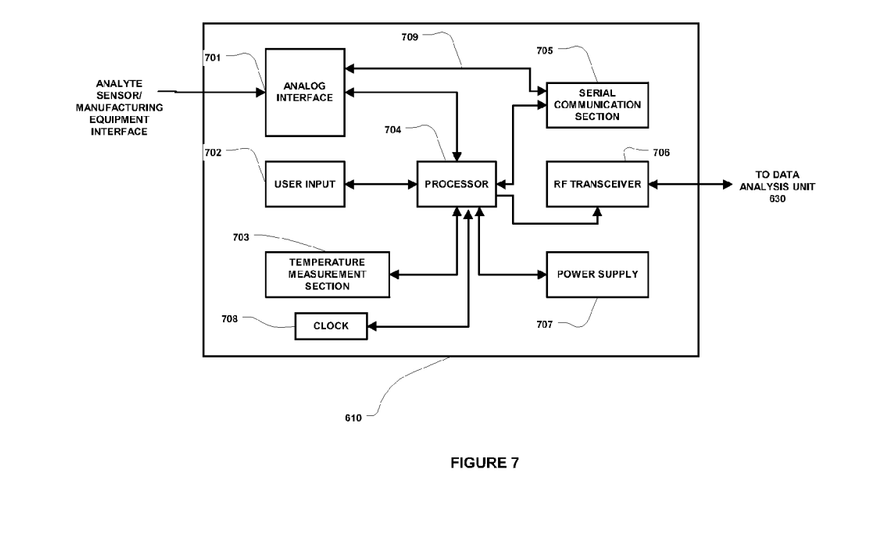
FIG. 7 illustrates a block diagram of the data processing unit of the integrated analyte sensor delivery and data processing unit in accordance with one embodiment of the present invention.

FIG. 7 illustrates a block diagram of the data processing unit of the integrated analyte sensor delivery and data processing unit in accordance with one embodiment of the present invention. Referring to FIGS. 1 and 7, the data processing unit 101 (FIG. 1) in one embodiment includes an analog interface 701 configured to communicate with the sensor 106 (FIG. 2), a user input 702, and a temperature detection section 703, each of which is operatively coupled to a data processing unit processor 704 such as one or more central processing units (CPUs) or equivalent microprocessor units.

Further shown in FIG. 7 are a transmitter serial communication section 705 and an RF transceiver 706, each of which is also operatively coupled to the processor 704. In one embodiment, the serial communication section 705 may be operatively coupled to the analog interface 706 via communication link 709. Moreover, a power supply 707 such as a battery is also provided in the data processing unit 101 to provide the necessary power for the components in the data processing unit 101. Additionally, as can be seen from the Figure, clock 708 is provided to, among others, supply real time information to the processor 704.

Referring back to FIG. 7, the power supply section 707 in one embodiment may include a rechargeable battery unit that may be recharged by a separate power supply recharging unit (for example, provided in the data analysis unit 630 (FIG. 6)) so that the data processing unit 101 may be powered for a longer period of usage time. In addition, the temperature measurement (or detection) section 703 of the transmitter unit 102 is configured to monitor the temperature of the skin near the sensor insertion site. The temperature reading may be used to adjust the analyte readings obtained from the analog interface 701.

In this manner, in one embodiment, the sensor detected analyte levels are provided to the data processing unit 101 of the integrated analyte sensor and data processing unit 100 (FIG. 1), for example, as current signals, and which are in turn, converted to respective digital signals for transmission (including, for example, RF transmission) to the data analysis unit 630, fluid delivery unit 670, and/or the data processing terminal 650 for further processing and analysis (including drug (e.g., insulin) therapy management, infusion control, and health monitoring and treatment, for example). That is, the monitored analyte data may be used by the patient and/or the patient's healthcare provider to modify the patient's therapy such as an infusion protocol (such as basal profile modifications in the case of diabetics) as necessary to improve insulin infusion therapy for diabetics, and further, to analyze trends in analyte levels for improved treatment.

Additional detailed description of the data monitoring and management system such as analyte monitoring systems, its various components including the functional descriptions of data processing unit and data analysis unit are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

In the manner described above, in one embodiment, the integrated analyte sensor and data processing unit assembly is configured to integrate an analyte sensor, a sensor introducer mechanism, and a data processing device into a single disposable assembly which allows for simple and accurate sensor deployment to the desired subcutaneous position, and which may be used with one hand by the user or the patient. Accordingly, a separate sensor introducing device such as a separate insertion gun or a separate sensor delivery mechanism is not necessary.

Furthermore, by integrating the analyte sensor, the introducer as well as the data processing unit into a single assembly, it is possible to have a smaller profile, simpler use application with less packaging thereby achieving cost reduction in manufacturing. Indeed, by reducing the number of components needed for sensor placement, within the scope of the present invention, other benefits such as reduction in material cost, weight, packaging, and associated handling and disposal may be achieved.

An apparatus including an analyte sensor and a data processing unit in accordance with one embodiment of the present invention includes a housing, a data processing unit coupled to the housing, an introducer removably coupled to the housing, the introducer including a first portion configured for piercing through a skin layer of a subject, and an analyte sensor coupled to the housing, the analyte sensor including a first portion and a second portion, the first portion of the analyte sensor coupled to the first portion of the introducer, and the second portion of the analyte sensor coupled to the data processing unit, where the first portion of the analyte sensor is configured for transcutaneous placement so as to be in fluid contact with an interstitial fluid of the subject, where the second portion of the analyte sensor is in electrical contact with the data processing unit, and further, where at least a portion of the data processing unit, at least a portion of the introducer and at least a portion of the analyte sensor are coupled to the housing as a single integrated assembly.

In one embodiment, there is further provided an adhesive layer substantially on a lower surface of the housing, the adhesive layer configured to removably attach the housing to the skin layer of the subject.

Additionally, a guard segment may be removably coupled to the first portion of the introducer, where the guard segment may be configured to substantially seal the first portion of the introducer.

In a further aspect, the first portion of the introducer may include a sharp tip for piercing through the skin layer of the subject, wherein when the sharp tip is pierced through the skin layer, the first portion of the analyte sensor is transcutaneously placed under the skin layer of the subject so as to be in fluid contact with the interstitial fluid of the subject.

In another aspect, the introducer may be configured to decouple from the housing after the first portion of the analyte sensor is transcutaneously positioned under the skin layer of the subject.

The analyte sensor may include a glucose sensor.

The data processing unit in one embodiment may include a data transmission unit configured to receive one or more signals associated with an analyte level of the subject from the analyte sensor, where the data transmission unit may be configured to wirelessly transmit data associated with the one or more signals received from the analyte sensor, where the data transmission unit may include an RF data transmission unit.

An integrated assembly in accordance with another embodiment of the present invention includes a housing, a data processing unit substantially disposed within the housing, an introducer removably coupled to the housing, at least a portion of the introducer disposed within the housing, and an analyte sensor coupled to the housing, a first portion of the analyte sensor configured for subcutaneous placement and in fluid contact with an interstitial fluid of a subject, and a second portion of the analyte sensor disposed within the housing and in electrical communication with the data processing unit.

The second portion of the analyte sensor in one embodiment may be permanently coupled to the data processing unit.

In another aspect, the introducer may be configured to decouple from the housing after the second portion of the analyte sensor is transcutaneously positioned under the skin layer of the subject.

An insertion kit in accordance with still another embodiment includes a housing, a data processing unit substantially disposed within the housing, an introducer removably coupled to the housing, at least a portion of the introducer disposed within the housing, and an analyte sensor coupled to the housing, a first portion of the analyte sensor configured for subcutaneous placement and in fluid contact with an interstitial fluid of a subject, and a second portion of the analyte sensor disposed within the housing and in electrical communication with the data processing unit.

In one embodiment, the introducer may be manually removed from the housing.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus comprising:
   a disposable assembly including:
      a housing;
      a data processing unit disposed in the housing;
      an introducer removably disposed within the housing and within the data processing unit, the introducer including a first portion having a sharp distal end configured for piercing through a skin layer of a subject, wherein the first portion of the introducer is removable from the housing after piercing through the skin layer of the subject; and
      an analyte sensor including a first portion and a second portion, the first portion of the analyte sensor coupled to the first portion of the introducer, and the second portion of the analyte sensor coupled to the data processing unit;
         wherein the first portion of the analyte sensor is configured for transcutaneous placement so as to be in fluid contact with an interstitial fluid of the subject;
         wherein the second portion of the analyte sensor is in electrical contact with the data processing unit prior to transcutaneous placement of the first portion of the analyte sensor; and
         wherein the housing, the data processing unit and the introducer are pre-assembled to form the disposable assembly, and the housing includes a self-sealing aperture through which the introducer is removable.

2. The apparatus of claim 1 further including an adhesive layer provided substantially on a lower surface of the housing, wherein the adhesive layer is configured to removably attach the housing to the skin of the subject.

3. The apparatus of claim 2, wherein the adhesive layer includes a removable protective layer.

4. The apparatus of claim 1 further comprising a guard segment removably coupled to the first portion of the introducer.

5. The apparatus of claim 1 wherein the first portion of the introducer includes a sharp tip for piercing through the skin of the subject, wherein when the sharp tip is pierced through the skin, the first portion of the analyte sensor is transcutaneously placed under the skin of the subject so as to be in fluid contact with the interstitial fluid of the subject.

6. The apparatus of claim 1 wherein the introducer is configured to decouple from the housing and the data processing unit after the first portion of the analyte sensor is transcutaneously positioned under the skin of the subject.

7. The apparatus of claim 1 wherein the data processing unit includes a data transmission unit configured to receive one or more signals associated with an analyte level of the subject from the analyte sensor.

8. The apparatus of claim 7 wherein the data transmission unit is configured to wirelessly transmit data associated with the one or more signals received from the analyte sensor.

9. The apparatus of claim 8 wherein the data transmission unit includes an RF data transmission unit.

10. The apparatus of claim 1, the housing including a lower surface having an adhesive layer disposed thereon, the adhesive layer provided with a removable protective layer thereon and an integrated guard segment covering the first portion of the introducer.

11. The apparatus of claim 1 wherein the introducer is positionable through the self-sealing aperture of the housing.

12. The apparatus of claim 1, wherein the second portion of the analyte sensor has a planar configuration.

13. The apparatus of claim 1, wherein the second portion of the analyte sensor extends substantially transverse to the first portion of the analyte sensor.

14. The apparatus of claim 1, wherein when the introducer is withdrawn from the self-sealing aperture, there is no opening in the housing through which moisture or contaminant can pass.

15. An integrated assembly, comprising:
   a housing;
   a data processing unit disposed within the housing;
   an introducer having at least a portion removably disposed within the housing and within the data processing unit, the introducer including a first portion having a sharp distal end configured for piercing through a skin layer of a subject, wherein the first portion of the introducer is removable from the housing after piercing through the skin layer of the subject; and
   an analyte sensor coupled to the housing, a first portion of the analyte sensor configured for subcutaneous placement and so as to be in fluid contact with an interstitial fluid of the subject, and a second portion of the analyte sensor disposed within the housing and in electrical communication with the data processing unit prior to subcutaneous placement of the first portion of the analyte sensor;
      wherein the housing, the data processing unit, the introducer, and the analyte sensor are pre-assembled as a single disposable unit, and the housing includes a self-sealing aperture through which the introducer is removable.

16. The assembly of claim 15 wherein the second portion of the analyte sensor is permanently coupled to the data processing unit.

17. The assembly of claim 15 wherein the introducer is configured to decouple from the housing and the data processing unit after the first portion of the analyte sensor is transcutaneously positioned under the skin of the subject.

18. The assembly of claim 15 wherein the data processing unit includes a data transmission unit configured to receive one or more signals associated with an analyte level of the subject from the analyte sensor.

19. The assembly of claim 18 wherein the data transmission unit is configured to wirelessly transmit data associated with the one or more signals received from the analyte sensor.

20. The assembly of claim 15 wherein the introducer is manually removable from the housing and the data processing unit.

21. The assembly of claim 15 further including an adhesive layer provided substantially on a lower surface of the housing, wherein the adhesive layer is configured to removably attach the housing to the skin of the subject.

22. The assembly of claim 15 further comprising a guard segment removably coupled to the first portion of the introducer.

23. The assembly of claim 15 wherein the introducer is positionable through the self-sealing aperture of the housing.

24. The assembly of claim 15 wherein an opening in the housing and in the data processing unit is configured to receive a first portion of the introducer.

25. The assembly of claim 15 wherein the introducer further includes a proximal portion configured for engaging an outer surface of the data processing unit.

26. The assembly of claim 15 wherein the first portion of the analyte sensor is coupled to a distal portion of the introducer, both portions extending from a lower surface of the housing.

27. The assembly of claim 15, wherein when the introducer is withdrawn from the self-sealing aperture, there is no opening in the housing through which moisture or contaminant can pass.

28. A method of monitoring an analyte within the interstitial fluid under the skin of a subject, the method comprising:

providing a pre-assembled integrated assembly comprising a housing and a data processing unit disposed within the housing, an introducer removably disposed at least partially within the housing and the data processing unit, and an analyte sensor disposed at least partially within a first portion of the introducer, the first portion of the introducer having a sharp distal end configured for piercing through the skin of the subject, wherein the housing includes a self-sealing aperture through which the introducer is removable;

positioning the integrated assembly at a target location on the skin of the subject;

using the first portion of introducer to transcutaneously position a portion of the sensor under the skin; and removing the first portion of introducer from the integrated assembly while the integrated assembly is maintained at the target location and the sensor is retained under the skin.

29. The method of claim 28, wherein a proximal portion of the introducer is disposed at an outer surface of the housing.

30. The method of claim 29, wherein the outer surface of the housing is a bottom surface and the portion of the introducer disposed therethrough includes the portion of the sensor disposed therein.

31. The method of claim 29, wherein the outer surface of the housing is an upper surface and the portion of the introducer disposed therethrough is configured for user insertion of the introducer through the skin surface.

32. The method of claim 31 further comprising, prior to transcutaneously positioning the analyte sensor, removing a guard segment from a sharp tip of the introducer.

33. The method of claim 28, wherein a portion of the analyte sensor which is not disposed within the introducer is in electrical contact with the data processing unit.

34. The method of claim 28, wherein the housing includes a lower surface having an adhesive layer disposed thereon wherein the adhesive layer is provided with a removable protective layer thereon, the method further comprising, prior to using the introducer to transcutaneously positioning the analyte sensor, removing the protective layer from the adhesive layer on the lower surface of the housing to expose the adhesive layer.

35. The method of claim 28, wherein when the introducer is withdrawn from the self-sealing aperture, there is no opening in the housing through which moisture or contaminant can pass.

* * * * *